(12) United States Patent
Ham

(10) Patent No.: US 9,161,730 B2
(45) Date of Patent: Oct. 20, 2015

(54) APPARATUS FOR DETECTING X-RAY, METHOD OF MANUFACTURING THE SAME, AND METHOD OF REPAIRING THE SAME

(71) Applicant: Samsung Display Co., Ltd., Yongin, Gyeonggi-Do (KR)

(72) Inventor: Hyung-Jin Ham, Yongin (KR)

(73) Assignee: SAMSUNG DISPLAY CO., LTD. (KR)

( * ) Notice: Subject to any disclaimer, the term of this patent is extended or adjusted under 35 U.S.C. 154(b) by 138 days.

(21) Appl. No.: 14/053,964

(22) Filed: Oct. 15, 2013

(65) Prior Publication Data

US 2014/0348303 A1  Nov. 27, 2014

(51) Int. Cl.

| | | |
|---|---|---|
| *A61B 6/14* | (2006.01) | |
| *H01L 21/52* | (2006.01) | |
| *H01L 23/32* | (2006.01) | |
| *H01L 27/146* | (2006.01) | |
| *H01L 27/148* | (2006.01) | |
| *A61B 6/00* | (2006.01) | |
| *G01T 1/24* | (2006.01) | |
| *G03B 42/04* | (2006.01) | |

(52) U.S. Cl.
CPC ............ *A61B 6/4283* (2013.01); *A61B 6/4233* (2013.01); *A61B 6/44* (2013.01); *A61B 6/4411* (2013.01); *G01T 1/244* (2013.01); *G03B 42/047* (2013.01); *H01L 27/14618* (2013.01); *A61B 6/42* (2013.01); *H01L 21/52* (2013.01); *H01L 23/32* (2013.01); *H01L 27/14601* (2013.01); *H01L 27/14683* (2013.01); *H01L 27/14806* (2013.01); *Y10T 29/49124* (2015.01)

(58) Field of Classification Search
CPC ............ A61B 6/00; A61B 6/14; A61B 6/145; A61B 6/42; A61B 6/4283; A61B 6/44; A61B 6/4411; G01T 1/243; G01T 1/244; H01L 21/52; H01L 23/32; H01L 23/48; H01L 23/481; H01L 23/482; H01L 23/4824; H01L 23/485; H01L 24/90; H01L 27/14; H01L 27/144; H01L 27/146; H01L 27/14601; H01L 27/14618; H01L 27/14636; H01L 27/14658; H01L 27/1465

USPC ............ 378/38, 91, 98.8, 189–191, 204, 210; 250/370.01, 370.08, 370.09, 370.11, 250/370.14, 371, 526

See application file for complete search history.

(56) References Cited

U.S. PATENT DOCUMENTS

| | | | |
|---|---|---|---|
| 2006/0169872 A1* | 8/2006 | Yoshimuta | 250/208.1 |
| 2012/0076266 A1 | 3/2012 | Kim et al. | |
| 2013/0259208 A1* | 10/2013 | Watanabe | 378/182 |

FOREIGN PATENT DOCUMENTS

| | | |
|---|---|---|
| KR | 1020070121983 A | 12/2007 |
| KR | 1020080000108 A | 1/2008 |
| KR | 1020080064656 A | 7/2008 |
| KR | 1020120028852 A | 3/2012 |

\* cited by examiner

*Primary Examiner* — Anastasia Midkiff
(74) *Attorney, Agent, or Firm* — Cantor Colburn LLP

(57) ABSTRACT

An X-ray detection apparatus including a case; a circuit board disposed in the case; a connection circuit unit disposed in the case, where the connection circuit unit is electrically connected with the circuit board and includes an integrated circuit ("IC") chip; a detection panel configured to be inserted into and ejected from the case, where the detection panel is electrically connected to the connection circuit unit; and a contact support unit disposed in the case, wherein the contact support unit allows the connection circuit unit and the detection panel to contact each other by applying a force on the connection circuit unit.

24 Claims, 8 Drawing Sheets

APPARATUS FOR DETECTING X-RAY, METHOD OF MANUFACTURING THE SAME, AND METHOD OF REPAIRING THE SAME

This application claims priority to Korean Patent Application No. 10-2013-0059932, filed on May 27, 2013, and all the benefits accruing therefrom under 35 U.S.C. §119, the content of which in its entirety is herein incorporated by reference.

BACKGROUND

1. Field

Exemplary embodiments of the invention relate to an apparatus for detecting X-ray, a method of manufacturing the apparatus for detecting X-ray, and a method of repairing the apparatus for detecting X-ray, and more particularly, to an apparatus for detecting X-ray with improved electrical characteristics, and a method of manufacturing the apparatus for detecting X-ray, and a method of repairing the apparatus for detecting X-ray with improved manufacturing characteristics and repairing characteristics.

2. Description of the Related Art

An X-ray detection apparatus is an apparatus that detects X-ray, which is a type of radiation, and has recently drawn attention as an apparatus for the medical industry.

Conventionally, an X-ray detection method using a separate film has been used. Such a conventional X-ray detection method may be used only when an immobile subject is exposed to the X-ray, and a new film is used to detect another X-ray.

Recently, a digital radiography ("DR") method using a detection panel, which is a type of flat display panel, has been used.

A detection panel typically includes a plurality of detection devices for detecting X-ray. Also, a circuit board, an integrated circuit ("IC") chip and the like for determining a value detected by the detection panel are disposed outside the detection panel.

Manufacturing characteristics of the X-ray detection apparatus may be deteriorated when the detection panel and the devices, such as the circuit board and the like outside the detection panel, are connected or attached to each other. Also, electrical characteristics of the X-ray detection apparatus may be deteriorated due to deterioration of connection characteristics between the detection panel and the devices, such as the circuit board outside the detection panel.

In addition, when a defect occurs in the detection panel while using the X-ray detection apparatus, some of parts of the X-ray detection apparatus that are typically in contact with and attached to the detection panel as well as the detection panel itself may be repaired.

SUMMARY

Exemplary embodiments of the invention provide an apparatus for detecting X-ray with improved electrical characteristics, and a method of manufacturing the apparatus for detecting X-ray, and a method of repairing the apparatus for detecting X-ray with improved manufacturing characteristics and repairing characteristics.

According to an exemplary embodiment of the invention, an X-ray detection apparatus includes a case, a circuit board disposed in the case, a connection circuit unit disposed in the case, where the connection circuit unit is electrically connected to the circuit board and includes an integrated circuit ("IC") chip, a detection panel configured to be inserted into and ejected from the case, where the detection panel is electrically connected to the connection circuit unit when the detection panel is inserted into the case; and a contact support unit disposed in the case, where the contact support unit allows the connection circuit unit and the detection panel to contact each other by applying a force on the connection circuit unit.

In an exemplary embodiment, when the detection panel is inserted into the case the contact support unit may substantially continuously apply the force onto the connection circuit unit such that a contact between the connection circuit unit and the detection panel is substantially maintained.

In an exemplary embodiment, the contact support unit may reduce the pressure applied to the connection circuit unit to remove the contact between the connection circuit unit and the detection panel to replace the detection panel.

In an exemplary embodiment, the contact support unit may include a press member which applies the force on a surface of the connection circuit unit.

In an exemplary embodiment, the press member may include a sensor which senses a distance and the pressure between the connection circuit unit and the detection panel.

In an exemplary embodiment, the contact support unit may further include a main body member, and an intermediate member which connects the main body member and the press member to each other, where the intermediate member may operate the press member.

In an exemplary embodiment, the main body member and the press member may be spaced apart from each other.

In an exemplary embodiment, the contact support unit may further include a connection member disposed between the press member and the intermediate member, and between the main body member and the intermediate member.

In an exemplary embodiment, the detection panel may include a pad unit, the connection circuit unit may include a contact surface, and the pad unit and the contact surface may contact each other by the contact support unit.

In an exemplary embodiment, the connection circuit unit may be bent such that opposing ends of the connection circuit unit face each other.

In an exemplary embodiment, the detection panel may be disposed in a space defined by an inner surface of the connection circuit unit, which is bent.

In an exemplary embodiment, the contact support unit may be disposed between an inner surface of the case and an upper outer surface of the connection circuit unit.

In an exemplary embodiment, the apparatus may further include a middle plate disposed between the circuit board and the detection panel.

In an exemplary embodiment, the detection panel may include a scintillator layer disposed on a surface of the detection panel, separate from the connection circuit unit.

In an exemplary embodiment, the apparatus may further include a scintillator disposed in the case and spaced apart from the connection circuit unit; and a press support unit disposed in the case, where the press support unit presses the scintillator toward the detection panel by pressing the scintillator when the detection panel is inserted into the case.

In an exemplary embodiment, the case may include a slot defined in a surface of the case, and the detection panel is inserted and ejected through the slot.

In an exemplary embodiment, the case may include a cover member, and the detection panel is housed in the case or ejected from the case by moving the cover member up or down.

According to another exemplary embodiment of the invention, a method of manufacturing an X-ray detection apparatus includes preparing a case including a circuit board, a connection circuit unit which is electrically connected to the circuit board and includes an integrated circuit chip, and a contact support unit; housing a detection panel in the case; and contacting the connection circuit unit and the detection panel each other by applying a pressure on the connection circuit unit through the contact support unit.

In an exemplary embodiment, the method may further include substantially continuously applying the pressure on the connection circuit unit through the contact support unit such that the contact support unit maintains a contact state between the detection panel and the connection circuit unit.

In an exemplary embodiment, the case further may include a scintillator and a press support unit, and the method may further include pressing the scintillator and the detection panel by applying a pressure on the scintillator through the pressure support unit when the detection panel is housed in the case.

According to another exemplary embodiment of the invention, a method of repairing an X-ray detection apparatus, where the X-ray detection apparatus includes a case, a circuit board disposed in the case, the connection circuit unit which is disposed in the case, is electrically connected to the circuit board, and includes an integrated circuit chip, a detection panel configured to be housed in and ejected from the case and is electrically connected to the connection circuit unit, and a contact support unit which is disposed in the case and applies a force onto the connection circuit unit to contact the connection circuit unit and the detection panel each other; where the method includes removing a contact between the connection circuit unit and the detection panel by removing a force applied to the connection circuit unit by the connection support unit, and ejecting the detection panel from the case.

In an exemplary embodiment, the method may further include housing a replacement detection panel in the case after the ejecting the detection panel from the case, and contacting the replacement detection panel and the connection circuit unit through the contact support unit.

In an exemplary embodiment, the case may further include a scintillator and a press support unit, and the scintillator is pressed toward the detection panel by the press support unit such that the scintillator and the detection panel contact each other.

In an exemplary embodiment, the method may further include removing a contact between the scintillator and the detection panel by reducing a pressure applied to the scintillator by the press support unit before the ejecting the detection panel from the case.

BRIEF DESCRIPTION OF THE DRAWINGS

The above and other features of the invention will become more apparent by describing in detail exemplary embodiments thereof with reference to the attached drawings, in which.

DETAILED DESCRIPTION

Figure 1:
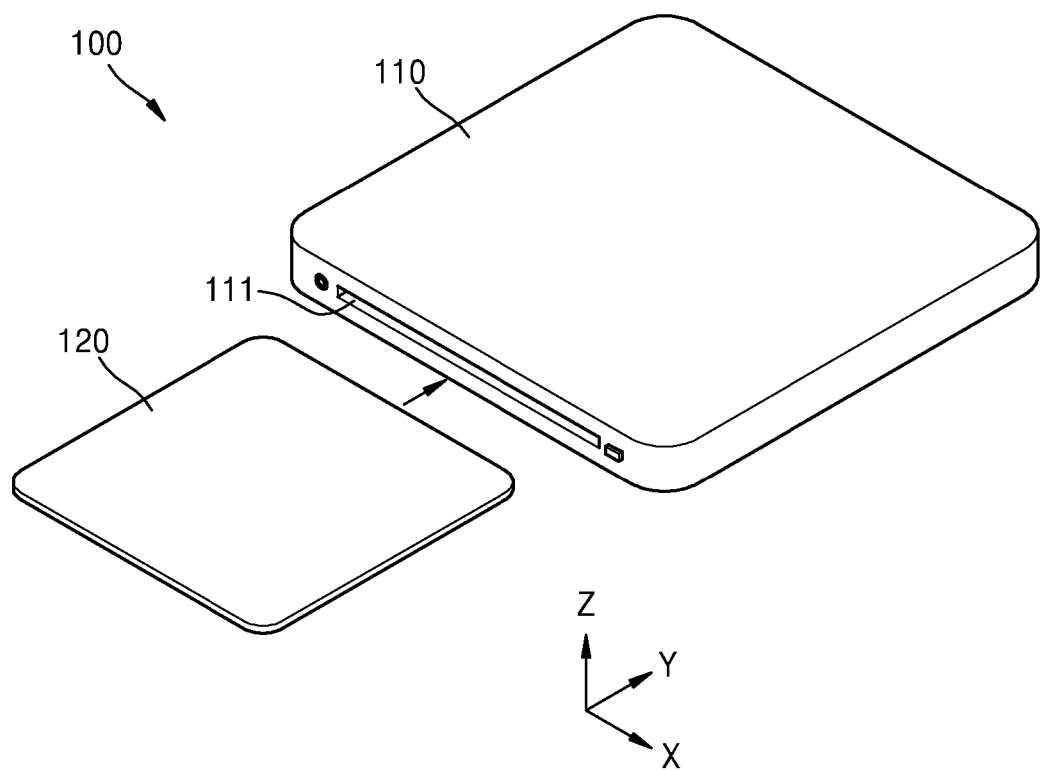
FIG. 1 is a perspective view of a final manufacturing process of an exemplary embodiment of an X-ray detection apparatus according to the invention.

The invention will be described more fully hereinafter with reference to the accompanying drawings, in which embodiments of the invention are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the claims set forth herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail by explaining embodiments of the invention with reference to the attached drawings.

Figure 2:
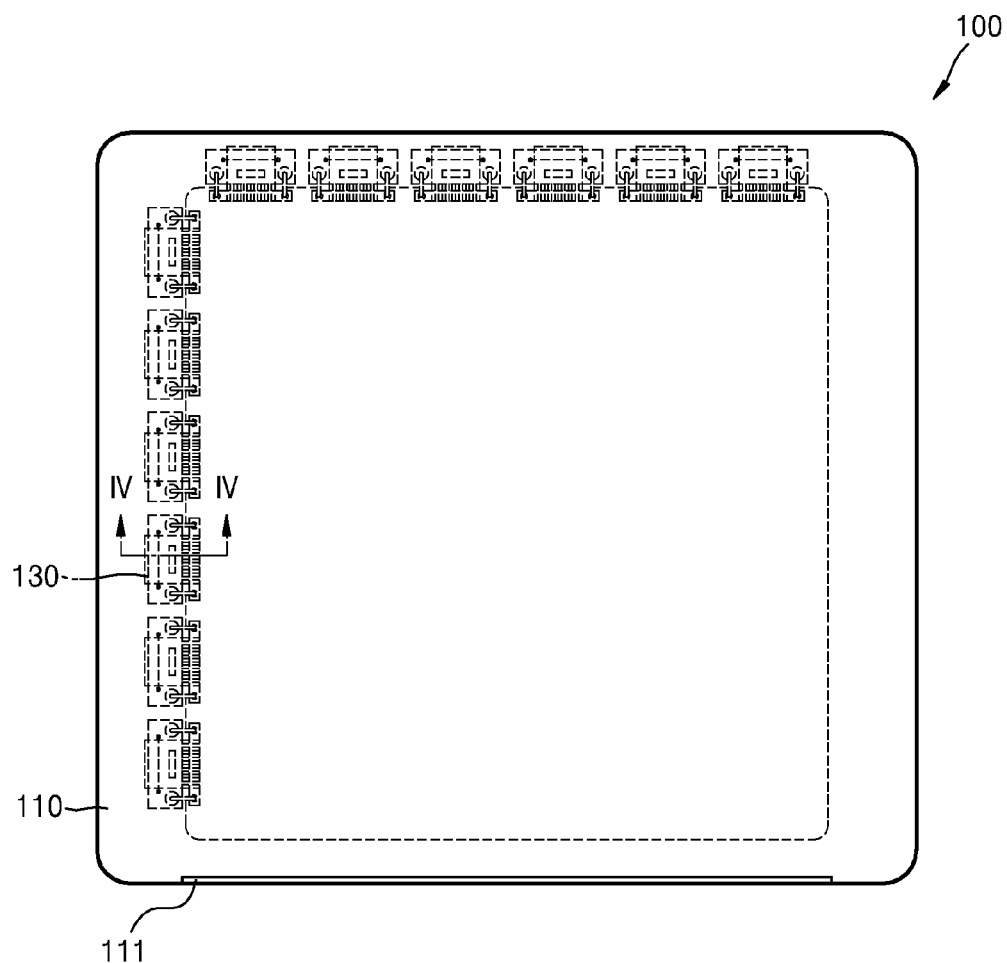
FIG. 2 is a see-through plan view of the X-ray detection apparatus of FIG. 1.
Figure 3:
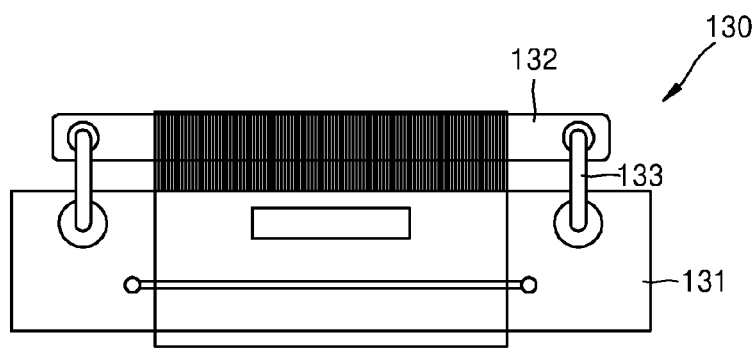
FIG. 3 is a view of an exemplary embodiment of a contact module of FIG. 2.
Figure 4:
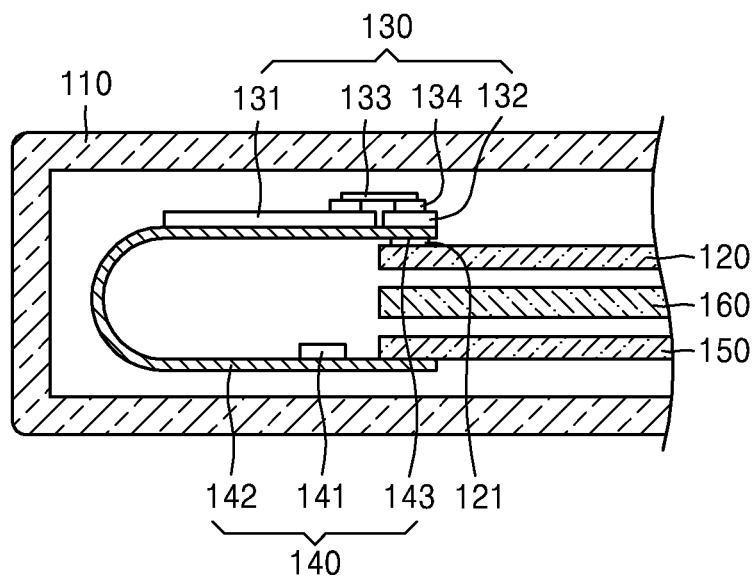
FIG. 4 is a cross-sectional view taken along line IV-IV of FIG. 2.

FIG. 1 is a perspective view of a final manufacturing process of an exemplary embodiment of an X-ray detection apparatus 100 according to the invention, FIG. 2 is a see-through plan view of the X-ray detection apparatus 100 of FIG. 1, FIG. 3 is a view of an exemplary embodiment of a contact support unit 130 of FIG. 2, and FIG. 4 is a cross-sectional view taken along line IV-IV of FIG. 2.

Referring to FIGS. 1 through 4, an exemplary embodiment of the X-ray detection apparatus 100 includes a case 110 and a detection panel 120.

The case 110 includes a slot 111, through which the detection panel 120 may be inserted or ejected. The slot 111 may be defined in a side of the case 110.

In a manufacturing process of the X-ray detection apparatus 100, the detection panel 120 may be disposed in, e.g., inserted into, the case 110 through the slot 111 and then disposed to be in contact with and coupled to a connection circuit unit 140 via a contact support unit 130 to complete the manufacturing process of the X-ray detection apparatus 100. An exemplary embodiment of the manufacturing process will be later described in detail.

In such an embodiment, when the detection panel 120 is defective, the detection panel 120 is ejected through the slot 111, and a replacement detection panel 120, which normally operates, may be inserted into the case 110 instead of the defective detection panel 120.

The contact support unit 130, the connection circuit unit 140, and a circuit board 150 are disposed in the case 110. In such an embodiment, once the detection panel 120 is inserted in the case 110, the manufacture of the X-ray detection apparatus 100 may be ultimately completed if a contacting process between the detection panel 120 and the connection circuit unit 140 is performed.

In an exemplary embodiment, as shown in FIG. 4, the contact support unit 130 is disposed near an upper interior surface of the case 110. In an exemplary embodiment, as shown in FIGS. 3 and 4, the contact support unit 130 includes a main body member 131, a press member 132, an intermediate member 133, and a connection member 134. In an exemplary embodiment, as shown in FIG. 2, a plurality of contact support units 130 may be included in the X-ray detection apparatus 100, and the number of contact support units 130 may be determined based on design conditions.

The main body member 131 maintains an overall intensity and a durability of the contact support unit 130. When the detection panel 120 is inserted into the case 110, the press member 132 presses the connection circuit unit 140 to connect a pad unit 121 of the detection panel 120 and the connection circuit unit 140. The press member 132 includes a sensor (not shown) that senses a distance and pressure between the connection circuit unit 140 and the detection panel 120, and thus allows the connection circuit unit 140 and the detection panel 120 to contact each other at a predetermined strength. In such an embodiment, the press member 132 continuously presses the connection circuit unit 140 with a predetermined pressure such that the contact circuit unit 140 and the detection panel 120 stably maintain a state of contacting and connecting with each other. In such an embodiment, the connection circuit unit 140 and the detection panel 120 are stably in contact with each other when the X-ray detection apparatus 100 is used.

In an exemplary embodiment, after continuous use of the X-ray detection apparatus 100, the detection panel 120 may be replaced when the detection panel 120 malfunctions or has a defect. In such an embodiment, the contact or connection between the detection panel 120 and the connection circuit unit 140 may be efficiently released by removing or reducing a pressure applied to the connection circuit unit 140 through the press member 132 of the contact support unit 130. When the detection panel 120 may be discharged from the case 110, a replacement detection panel 120 may be inserted into the case 110, and then the replacement detection panel 120 may be disposed to be in contact with and coupled to the connection circuit unit 140 through the contact support unit 130.

The intermediate member 133 connects the main body member 131 and the press member 132. The intermediate member 133 may drive the press member 132 to move in a direction toward the detection panel 120, e.g., downwardly, when the detection panel 120 is inserted. Although not shown in FIGS. 1 to 4, in an exemplary embodiment, the intermediate member 133 may automatically drive the press member 132 when the detection panel 120 is inserted. In such an embodiment, when insertion of the detection panel 120 is sensed through the sensor included in the press member 132 as described above, the intermediate member 133 may automatically drive the press member 132 to move in the direction toward the detection panel 120.

In an alternative exemplary embodiment of the invention, the operation of the press member 132 may be performed by control of a user from the outside of the case 110.

The press member 132 and the intermediate member 133 are connected to each other by the connection member 134, and the main body member 131 and the intermediate member 133 are connected to each other by the connection member 134. In such an embodiment, a driving force is selectively transferred only to the press member 132 to move the connection circuit unit 140. In an alternative exemplary embodiment, a driving force may be transferred to both the press member 132 and the main body member 131.

The circuit board 150 is disposed near a lower inner surface of the case 110. One or more electronic devices may be disposed on the circuit board 150. In one exemplary embodiment, for example, a timing controller, a power generating device, and an alternating current-to-direct current ("AC-DC") converter may be disposed on the circuit board 150.

The connection circuit unit 140 is disposed near a lower inner surface of the case 110 and connected to the circuit board 150. The connection circuit unit 140 includes a flexible member 142, an integrated circuit ("IC") chip 141 and a contact surface 143.

A surface of the flexible member 142 is connected to the circuit board 150, and thus the circuit board 150 and the connection circuit unit 140 are electrically connected. An exemplary embodiment of the flexible member 142 will be later described in detail.

In an exemplary embodiment, the flexible member 142 has flexibility, and thus both ends of the flexible member 142 may be bent. In such an embodiment, one end (e.g., a first end) and the other end (e.g., a second end) of the flexible member 142 are bent to face each other, and thus when the detection panel 120 is inserted into the case 110, the detection panel 120 is disposed in a space defined by an inner curved surface of the flexible member 142, e.g., a space between the one end and the other end of the flexible member 142 that are bent to face each other.

The IC chip 141 may perform various electrical functions and, for example, may function as an output device. In one exemplary embodiment, for example, the IC chip 141 may convert and output an electrical signal that is detected by the detection panel 120.

The contact surface 143 is a portion of an inner surface of the connection circuit unit 140 that contacts the detection panel 120. In such an embodiment, when the contact surface 143 and the detection panel 120 contact each other, the detection panel 120 and the connection circuit unit 140 are electrically connected.

A middle plate 160 may be further disposed on the circuit board 150. In an exemplary embodiment, the middle plate 160 is attached to the circuit board 150 by an attaching member (not shown), such as double-sided tape, for example. In such an embodiment, when the detection panel 120 is inserted into the case 110, the detection panel 120 is disposed on the middle plate 160, and the middle plate 160 is disposed between the circuit board 150 and the detection panel 120. In such an embodiment, the middle plate 160 effectively prevents damaging an upper surface of the circuit board 150 when the detection panel 120 is inserted, and allows efficient release of heat generated from the detection panel 120. In such an embodiment, the middle plate 160 supports a lower surface of the detection panel 120 such that the connection circuit unit 140 and the detection panel 120 may effectively contact and maintain an attached state when the contact support unit 130 presses the connection circuit unit 140.

Figure 5A:
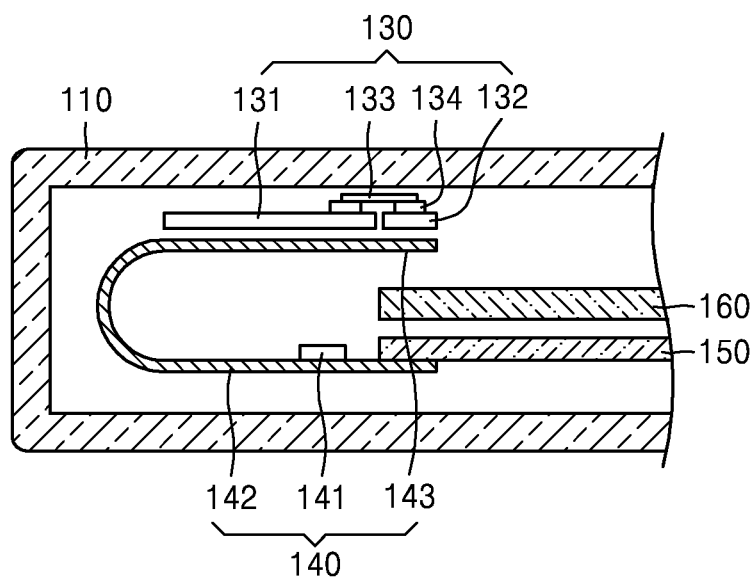
FIGS. 5A and 5B are cross-sectional views showing an operation of the contact module of the X-ray detection apparatus of FIG. 1.
Figure 5B:
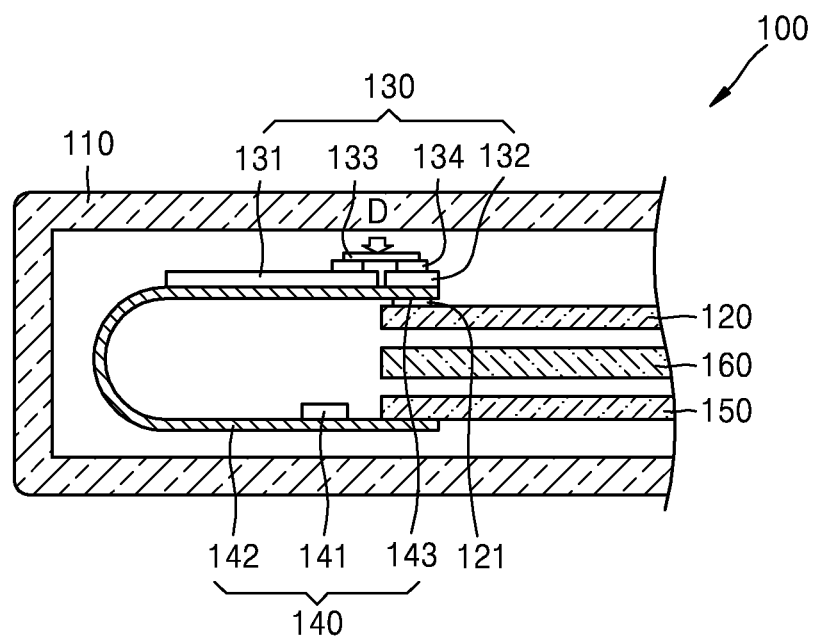

FIGS. 5A and 5B are cross-sectional views showing an operation of the contact support unit 130 of the X-ray detection panel 100 of FIG. 1.

An exemplary embodiment of the X-ray detection apparatus 100 is completely manufactured through an assembly process of the case 110 and the detection panel 120. The assembly process will be described later in detail.

First, FIG. 5A is a cross-sectional view of the case 110. FIG. 5A shows the case 110 before inserting the detection panel 120 therein. In an exemplary embodiment, as shown in FIG. 5A, the case 110 includes the contact support unit 130, the connection circuit unit 140, the circuit board 150 and the middle plate 160.

Before the inserting the detection panel 120, an end of the connection circuit unit 140 is connected to the circuit board 150 in the case 110, and the middle plate 160 is disposed on a surface of the circuit board 150. In one exemplary embodiment, the middle plate 160 may be attached to the surface of the circuit board 150 by double-sided tape (not shown).

The contact surface 143 of the connection circuit unit 140 is spaced apart from the middle plate 160 by a predetermined gap.

In an exemplary embodiment, as shown in FIG. 5A, the contact support unit 130 is spaced apart from the connection circuit unit 140. However, the invention is not limited thereto, and the connection circuit unit 140 and the contact support unit 130 may partially contact each other in an alternative exemplary embodiment.

Then, referring to FIG. 5B, the detection panel 120 is inserted into the case 110, and thus the X-ray detection apparatus 100, including the case 110 and the detection panel 120, is completely manufactured.

When the detection panel 120 is inserted into the case 110 through the slot 111 of the case 110, the detection panel 120 is disposed to correspond to the space between the middle plate 160 and the contact surface 143 of the connection circuit unit 140. In such an embodiment, a position and a size of the slot 111 may be determined to allow the slot 111 to function as a guide member of the detection panel 120. In an alternative exemplary embodiment, an additional guide member (not shown) for the detection panel 120 may be disposed inside the case 110.

When the detection panel 120 is inserted into the case 110 and disposed in a predetermined position, the contact support unit 130 operates. In such an embodiment, the press member 132 moves downward, e.g., in a direction from an inner upper surface of the case 110 to an inner lower surface of the case 110 as shown by arrow D of FIG. 5B (hereinafter, will be referred to as the "direction of arrow D), by an operation of the intermediate member 133. As the press member 132 gradually moves downward, the press member 132 contacts the flexible member 142, and the press member 132 presses the flexible member 142 in a direction toward the detection panel 120 as the press member 132 moves further down. In such an embodiment, the press member 132 applies a predetermined pressure on the connection circuit unit 140 such that the contact surface 143 stably contacts the pad unit 121 of the detection panel 120.

As a result, the detection panel 120 is electrically connected to the connection circuit unit 140, and thus the X-ray detection apparatus 100 is completely manufactured.

Figure 6:
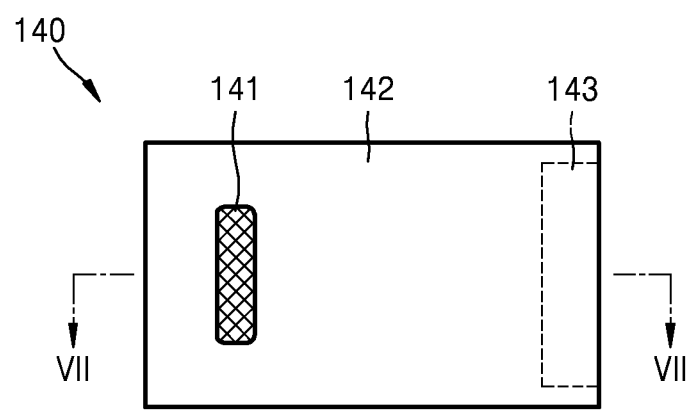
FIG. 6 is a plan view of an exemplary embodiment of a connection circuit unit of FIG. 4.
Figure 7:
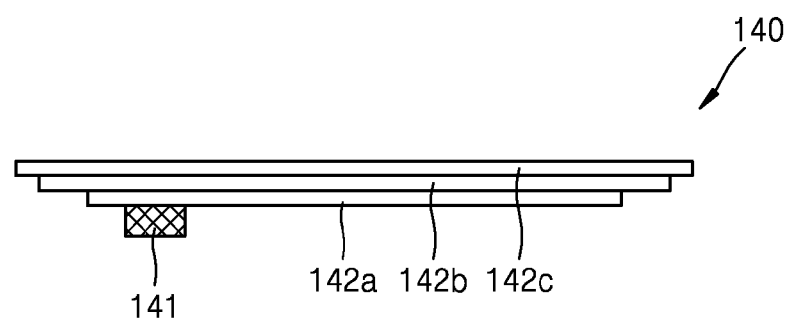
FIG. 7 is a cross-sectional view taken along line VII-VII of FIG. 6.

FIG. 6 is a plan view of the connection circuit unit 140 of FIG. 4, and FIG. 7 is a cross-sectional view taken along line VII-VII of FIG. 6. For convenience in description, FIGS. 6 and 7 show an exemplary embodiment of the connection circuit unit 140 having a flat shape before being bent.

In such an embodiment of the connection circuit unit 140, the IC chip 141 is disposed on a surface of the flexible member 142, and the contact surface 143 is defined by a portion of the surface of the flexible member 142 of the connection circuit unit 140. In such an embodiment, the contact surface 143 may be defined by a portion of a surface of two opposing surfaces of the flexible member 142, on which the IC chip 141 is disposed.

In such an embodiment, the flexible member 142 may include a plurality of layers. In one exemplary embodiment, for example, the flexible member 142 may include a protection film 142c, a resist layer 142a, and a conductive layer 142b disposed between the resist layer 142a and the conductive layer 142b, as shown in FIG. 7.

The portion of the flexible member 142 that defines the contact surface 143 may include the conductive layer 142b, such that the conductive layer 142b may contact the pad unit 121 of the detection panel 120.

The connection circuit unit 140 may be one of chip-on-film ("COF") type, flexible printed circuit ("FPC") type, and various other types.

Figure 8:
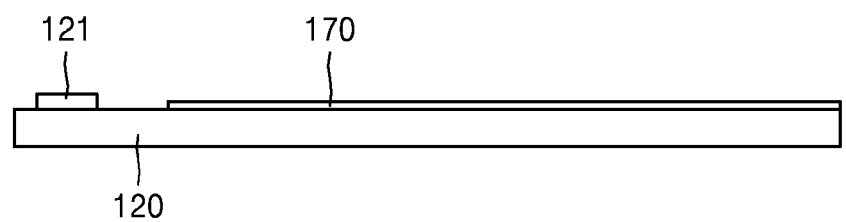
FIG. 8 is a side view of a detection panel of FIG. 4.

FIG. 8 is aside view of the detection panel 120 of FIG. 4.

In an exemplary embodiment, as shown in FIG. 8, the pad unit 121 is disposed on a surface of the detection panel 120. In such an embodiment, the detection panel 120 includes a scintillator layer 170.

The detection panel 120 may include a photodetector (not shown) and an electric device (not shown) connected to the photodetector. In one exemplary embodiment, for example, the detection panel 120 may include a photodiode (not shown), which detects X-ray, and a thin film transistor (not shown) and a plurality of signal wirings (not shown) that are electrically connected to the photodiode.

The scintillator layer 170 converts X-ray into light that may be detected relatively effectively such that the detection panel 120 substantially effectively detects X-ray. In one exemplary embodiment, for example, the scintillator layer 170 may convert X-ray into green light.

In an exemplary embodiment, the X-ray detection apparatus 100 includes the case 110 and the detection panel 120. When the detection panel 120 is inserted into the case 110, the detection panel 120 is electrically connected to the connection circuit unit 140 by the contact support unit 130, and a connect between the detection panel 120 and the connection circuit unit 140, e.g., an attachment between the detection panel 120 and the connection circuit unit 140, may be effectively maintained. In such an embodiment, when the detection panel 120 malfunctions or has a defect, the contact and connection between the detection panel 120 and the connection circuit unit 140 is efficiently released by removing the pressure applied onto the connection circuit unit 140 by the contact support unit 130, and thus the detection panel 120 may be ejected from the case 110. Then, a replacement detection panel 120 is inserted into the case 110 and connected to the connection circuit unit 140 through the contact support unit 130.

In an exemplary embodiment, the contact and connection between the detection panel 120 and the connection circuit unit 140 are simply performed through the contact support unit 130 such that the X-ray detection apparatus 100 may be provided by a simple manufacturing process thereof. In such an embodiment, electrical characteristics of the X-ray detection apparatus 100 may be substantially improved by effectively preventing detachment between the connection circuit unit 140 and the detection panel 120 using the pressure continuously applied on the connection circuit unit 140 by the contact support unit 130.

In such an embodiment, when the detection panel 120 is not working properly, the X-ray detection apparatus 100 may be efficiently repaired by simply replacing the detection panel 120. In such an embodiment, the connection circuit unit 140 that is connected with the detection panel 120 may be easily disconnected and separated from the detection panel 120 without replacing and repairing the connection circuit unit 140, and thus manufacturing and operating efficiencies of the X-ray detection apparatus 100 may be increased.

Figure 9:
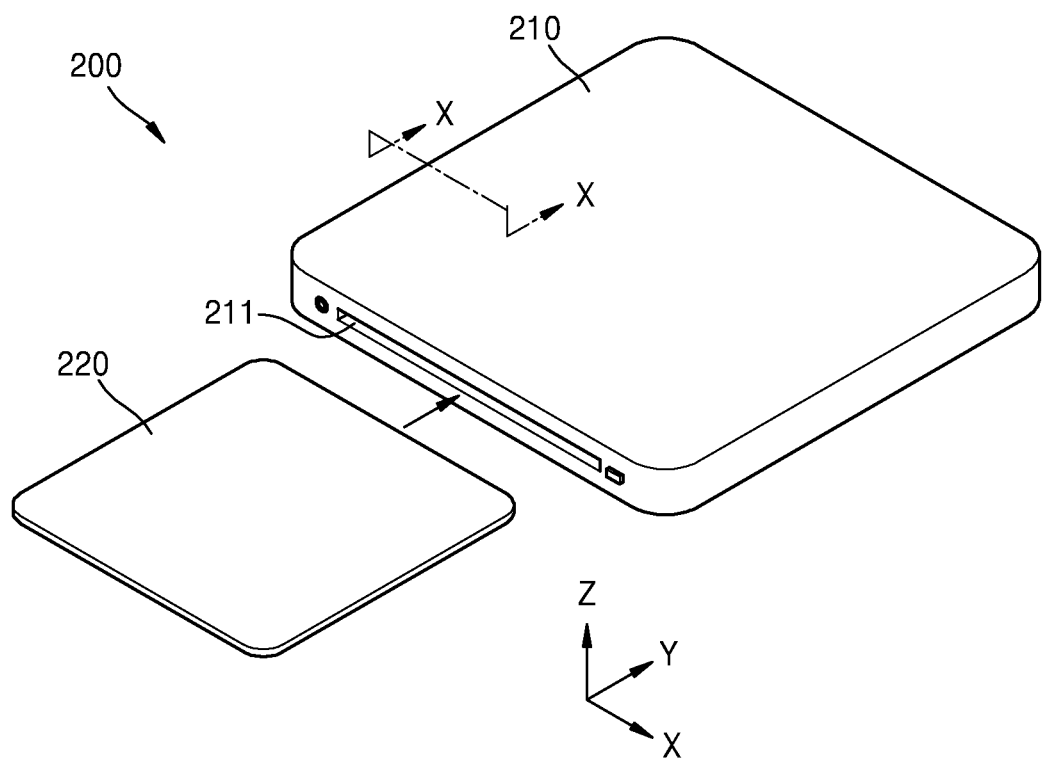
FIG. 9 is a perspective view of a final manufacturing process of an alternative exemplary embodiment of an X-ray detection apparatus according to the invention.
Figure 10:
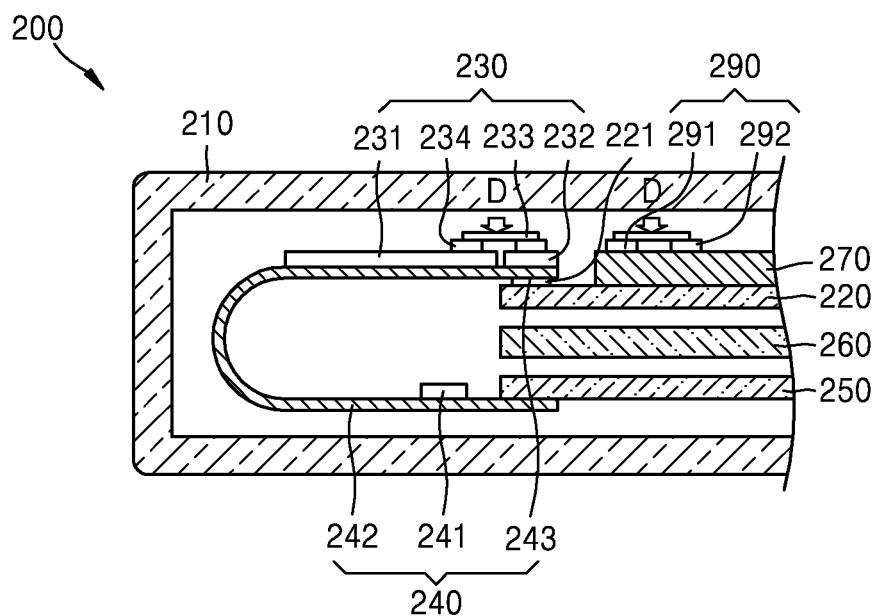
FIG. 10 is a cross-sectional view taken along line X-X of FIG. 9.

FIG. 9 is a perspective view of a final manufacturing process of an alternative exemplary embodiment of an X-ray detection apparatus 200 according to the invention, and FIG. 10 is a cross-sectional view taken along line X-X of FIG. 9. The X-ray detection apparatus 200 in FIG. 9 is substantially the same as the X-ray detection apparatus 100 shown in FIG. 1 except for the scintillator layer, and any repetitive detailed description thereof may be omitted or simplified.

In an alternative exemplary embodiment, as shown in FIG. 9, the X-ray detection apparatus 200 includes a case 210 and a detection panel 220. When the detection panel 220 is inserted into the case 210, the detection panel 220 is electrically connected to the connection circuit unit 240 by the contact support unit 230, and a connect between the detection panel 220 and the connection circuit unit 240, e.g., an attachment between the detection panel 220 and the connection circuit unit 240, may be effectively maintained.

In such an embodiment, the contact support unit 230 includes a main body member 231, a press member 232, an intermediate member 233, and a connection member 234. In such an embodiment, the connection circuit unit 240 includes a flexible member 242, an IC chip 241 and a contact surface 243. When the detection panel 220 is inserted into the case 210, the press member 232 presses the connection circuit unit 240 to connect a pad unit 221 of the detection panel 220 and the connection circuit unit 240.

In an exemplary embodiment, as shown in FIG. 1, the scintillator layer 170 may be disposed on a surface of the detection panel 120. In an alternative exemplary embodiment, as shown in FIG. 10, a scintillator 270 may be disposed in the case 210.

In such an embodiment, after the detection panel 220 is inserted into the case 210, when the detection panel 220 is electrically connected to a connection circuit unit 240, the scintillator 270 that is disposed in the case 210 is pressed against the detection panel 220, and thus the manufacture of the X-ray detection apparatus 200 of the embodiment is finally completed.

In such an embodiment, the scintillator 270 is disposed opposite to and spaced apart from a middle plate 260 in the case 210 and may be spaced apart from the connection circuit unit 240.

In such an embodiment, the X-ray detection apparatus may include a press support unit 290 disposed on an upper surface of the scintillator 270. The press support unit 290 includes a first press unit 291 and a second press unit 292. In such an embodiment, the first press unit 291 and the second press unit 292 may be spaced apart from each other, and a pressure applied on the scintillator 270 by the first press unit 291 may be different from a pressured applied on the scintillator 270 by the second press unit 292. However, the invention is not limited thereto, and the press support part 290 may include a single press unit, which is integrally formed as a single unitary and indivisible unit.

When the detection panel 220 is inserted into the case 210, the detection panel 220 and the connection circuit unit 240 are electrically connected to each other by an operation of a contact support unit 230. The operation of the contact support unit 230 is substantially the same as the exemplary embodiments described above, and thus any repetitive detailed description thereof will now be omitted.

In such an embodiment, when the detection panel 220 is inserted into the case 210, the press support unit 290 may operate in substantially the same manner as the contact support unit 230 operates. In such an embodiment, the press support unit 290 moves in the direction of arrow D to move the scintillator 270. The scintillator 270 moves in the direction of arrow D, e.g., a direction toward the detection panel 220, which is inserted into the case 210. The press support unit 290 applies a predetermined pressure onto the scintillator 270 such that the scintillator 270 and the detection panel 220 may be pressed toward each other, and the pressed state thereof may be effectively maintained.

The detection panel 220 may be effectively maintained in a predetermined position in the case 210 by the pressing between the detection panel 220 and the scintillator 270, such that a luminance efficiency of the X-ray detection apparatus 200 substantially improves, and an X-ray detective efficiency and accuracy of the X-ray detection apparatus 200 is thereby improved.

In such an embodiment, when the detection panel 220 has a defect, the detection panel 220 may be replaced with a replacement detection panel 220 that does not include a scintillator layer thereon by separating the detection panel 220 from the scintillator 270, such that cost of replacing the detection panel 220 is substantially reduced by reducing a manufacturing cost of the replacement detection panel.

Figure 11:
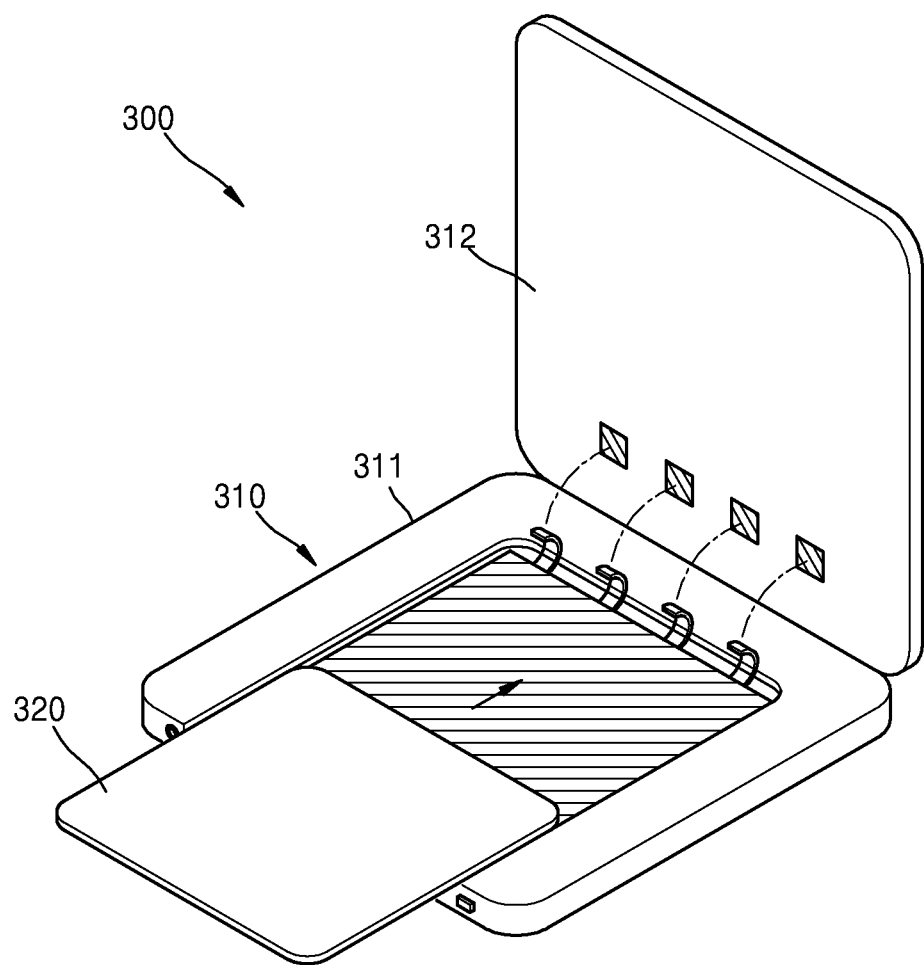
FIG. 11 is a perspective view of a final manufacturing process of another alternative exemplary embodiment of an X-ray detection apparatus according to the invention.

FIG. 11 is a perspective view of a final manufacturing process of another alternative exemplary embodiment of an X-ray detection apparatus 300 according to the invention. The X-ray detection apparatus 300 in FIG. 11 is substantially the same as the X-ray detection apparatus 100 or 200 shown in FIG. 1 or FIG. 9 except for the case, and any repetitive detailed description thereof may be omitted or simplified.

In such an embodiment, as described above, a detection panel 320 is inserted into a case 310, and the detection panel 320 and the case 310 are assembled, thereby completing the manufacture of the X-ray detection apparatus 300.

In such an embodiment, the case 310 includes a housing unit 311 and a cover unit 312. The detection panel 320 is inserted and housed in the housing unit 311, and the cover unit 312 covers the detection panel 320 when the detection panel 320 is inserted in the housing unit 311.

Although not shown in the drawing, when the detection panel 320 is housed in the housing unit 311, the detection panel 320 is disposed in a space defined between a middle plate (not shown) and a contact surface (not shown) of a connection circuit unit (not shown), the detection panel 320 is stably in contact with the connection circuit unit (not shown) by an operation of a contact support unit (not shown), and such a contact state is maintained. The operation of the detection panel 320 by the contact support unit (not shown) is substantially the same as the exemplary embodiments described above, and thus any repetitive detailed description thereof will be omitted.

While the invention has been particularly shown and described with reference to exemplary embodiments thereof, it will be understood by those of ordinary skill in the art that various changes in form and details may be made therein without departing from the spirit and scope of the invention as defined by the following claims.

What is claimed is:

1. An X-ray detection apparatus comprising:
a case;
a circuit board disposed in the case;
a connection circuit unit disposed in the case, wherein the connection circuit unit is electrically connected to the circuit board and comprises an integrated circuit chip;
a detection panel configured to be inserted into and ejected from the case, wherein the detection panel is electrically connected to the connection circuit unit when the detection panel is inserted into the case; and
a contact support unit disposed in the case, wherein the contact support unit allows the connection circuit unit and the detection panel to contact each other by applying a force on the connection circuit unit.

2. The apparatus of claim 1, wherein
when the detection panel is inserted into the case, the contact support unit substantially continuously applies the force onto the connection circuit unit such that a contact between the connection circuit unit and the detection panel is substantially maintained.

3. The apparatus of claim 1, wherein
when the detection panel is ejected from the case, the contact support unit reduces the force applied to the connection circuit unit to remove a contact between the connection circuit unit and the detection panel.

4. The apparatus of claim 1, wherein the contact support unit comprises a press member which applies the force on a surface of the connection circuit unit.

5. The apparatus of claim 4, wherein the press member comprises a sensor which senses a distance and a pressure between the connection circuit unit and the detection panel.

6. The apparatus of claim 4, wherein the contact support unit further comprises:
a main body member; and
an intermediate member which connects the main body member and the press member to each other,
wherein the intermediate member operates the press member.

7. The apparatus of claim 6, wherein the main body member and the press member are spaced apart from each other.

8. The apparatus of claim 6, wherein the contact support unit further comprises a connection member disposed between the press member and the intermediate member, and between the main body member and the intermediate member.

9. The apparatus of claim 1, wherein
the detection panel comprises a pad unit,
the connection circuit unit comprises a contact surface, and
the pad unit and the contact surface contact each other by the contact support unit.

10. The apparatus of claim 1, wherein the connection circuit unit is bent such opposing ends of the connection circuit unit face each other.

11. The apparatus of claim 10, wherein the detection panel is disposed in a space defined by an inner surface of the bent connection circuit unit.

12. The apparatus of claim 1, wherein the contact support unit is disposed between an inner surface of the case and an upper outer surface of the connection circuit unit.

13. The apparatus of claim 1, further comprising:
a middle plate disposed between the circuit board and the detection panel.

14. The apparatus of claim 1, wherein the detection panel comprises a scintillator layer disposed on a surface of the detection panel.

15. The apparatus of claim 1, further comprising:
a scintillator disposed in the case and spaced apart from the connection circuit unit; and
a press support unit disposed in the case, wherein the press support unit presses the scintillator toward the detection panel when the detection panel is inserted into the case.

16. The apparatus of claim 1, wherein
the case comprises a slot defined in a surface of the case, and
the detection panel is inserted and ejected through the slot.

17. The apparatus of claim 1, wherein
the case comprises a cover member, and
the detection panel is inserted in the case or ejected from the case by moving the cover member up or down.

18. A method of manufacturing an X-ray detection apparatus, the method comprising:
preparing a case comprising a circuit board, a connection circuit unit electrically connected to the circuit board and comprising an integrated circuit chip, and a contact support unit;
housing a detection panel in the case; and
contacting the connection circuit unit and the detection panel to each other by applying a pressure on the connection circuit unit through the contact support unit.

19. The method of claim 18, further comprising:
substantially continuously applying the pressure on the connection circuit unit through the contact support unit such that the contact support unit maintains a contact state between the detection panel and the connection circuit unit.

20. The method of claim 18, wherein
the case further comprises a scintillator and a press support unit, and
the method further comprises pressing the scintillator and the detection panel by applying a pressure on the scintillator through the pressure support unit when the detection panel is housed in the case.

21. A method of repairing an X-ray detection apparatus, wherein the X-ray detection apparatus comprises a case, a circuit board disposed in the case, a connection circuit unit disposed in the case and electrically connected to the circuit board, and which comprises an integrated circuit chip, a detection panel configured to be housed in and ejected from the case and which is electrically connected to the connection circuit unit, and a contact support unit disposed in the case and which applies a force onto the connection circuit unit to contact the connection circuit unit and the detection panel each other;
the method comprising:
removing a contact between the connection circuit unit and the detection panel by decreasing a force applied to the connection circuit unit by the connection support unit; and
ejecting the detection panel from the case.

22. The method of claim 21 further comprising:
housing a replacement detection panel in the case after the ejecting the detection panel from the case; and
contacting the replacement detection panel and the connection circuit unit through the contact support unit.

23. The method of claim 21, wherein
the case further comprises a scintillator and a press support unit, and
the scintillator is pressed toward the detection panel by the press support unit such that the scintillator and the detection panel contact each other.

24. The method of claim 23 further comprising:
removing a contact between the scintillator and the detection panel by reducing a pressure applied to the scintillator by the press support unit before the ejecting the detection panel from the case.

* * * * *